US012507867B2

(12) United States Patent
Mueller et al.

(10) Patent No.: US 12,507,867 B2
(45) Date of Patent: Dec. 30, 2025

(54) MEDICAL INSTRUMENT

(71) Applicant: Erbe Elektromedizin GmbH, Tuebingen (DE)

(72) Inventors: Marc Mueller, Nagold (DE); Frederik Kleber, Wannweil (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 503 days.

(21) Appl. No.: 17/985,691

(22) Filed: Nov. 11, 2022

(65) Prior Publication Data

US 2023/0148838 A1 May 18, 2023

(30) Foreign Application Priority Data

Nov. 18, 2021 (EP) .................................... 21209026

(51) Int. Cl.
*A61B 1/00* (2006.01)
*A61B 1/015* (2006.01)
(Continued)

(52) U.S. Cl.
CPC ...... *A61B 1/00096* (2013.01); *A61B 1/00165* (2013.01); *A61B 1/015* (2013.01);
(Continued)

(58) Field of Classification Search
CPC . A61B 1/00096; A61B 1/00165; A61B 1/015; A61B 1/00137; A61B 2018/00982; A61M 2025/0079
See application file for complete search history.

(56) References Cited

U.S. PATENT DOCUMENTS 4,240,434 A * 12/1980 Newkirk ............... A61F 2/2412 604/9
4,436,087 A * 3/1984 Ouchi ............... A61M 25/0133 600/153

(Continued)

FOREIGN PATENT DOCUMENTS

AU 2019204666 B2 4/2021
CN 101588765 A 11/2009

(Continued)

*Primary Examiner* — Timothy J Neal
(74) *Attorney, Agent, or Firm* — Blank Rome LLP

(57) ABSTRACT

An instrument according to the invention for medical or surgical treatment of a human or animal patient comprises at least one tool suitable for influencing a patient, e.g. an electrode, which is or are located in the field of view of an optical element. The optical element is arranged inside a channel in which a fluid flow can be maintained or can be caused in distal direction. The light passage window of optical element is offset relative to the distal opening of channel in proximal direction. A closure device is arranged between light passage window and opening of channel, which blocks passage of substances, particularly passage of liquid droplets and particles, from the opening to the light passage window as long as it is in closed position. If the closure device is open, it unblocks the fluid path and the light path between the light passage window to the opening. Preferably the closure device is controlled pneumatically by means of the liquid or gaseous fluid flowing inside channel. With this measure a contamination of the light passage window during operation of the instrument can be reliably avoided or at least reduced to a minor degree.

14 Claims, 3 Drawing Sheets

(51) Int. Cl.

| | |
|---|---|
| ***A61B 18/14*** | (2006.01) |
| *A61B 18/00* | (2006.01) |
| *A61M 25/00* | (2006.01) |

(52) U.S. Cl.

CPC ................................ *A61B 18/1492* (2013.01); *A61B 2018/00982* (2013.01); *A61M 2025/0079* (2013.01)

(56) References Cited

U.S. PATENT DOCUMENTS

| | | | | |
|---|---|---|---|---|
| 4,655,219 | A * | 4/1987 | Petruzzi ............. | A61B 17/2909 606/206 |
| 7,993,339 | B2 | 8/2011 | Kühner | |
| 2002/0029006 | A1 | 3/2002 | Turturro et al. | |
| 2005/0085694 | A1 | 4/2005 | Nakao | |
| 2008/0255424 | A1* | 10/2008 | Durgin ............... | A61B 10/0283 600/156 |
| 2012/0289954 | A1 | 11/2012 | Lam | |
| 2020/0237421 | A1 | 7/2020 | Ataman et al. | |

FOREIGN PATENT DOCUMENTS

| | | | |
|---|---|---|---|
| CN | 106255448 | A | 12/2016 |
| CN | 113208664 | A | 8/2021 |
| DE | 20118167 | U1 | 2/2002 |
| EP | 2 113 190 | A1 | 11/2009 |
| EP | 1 773 223 | B1 | 3/2011 |
| EP | 3 195 824 | A1 | 7/2017 |
| JP | S54123279 | A | 9/1979 |
| JP | S56155810 | U | 11/1981 |
| JP | S62113501 | U | 7/1987 |
| JP | H0743621 | A | 2/1995 |
| JP | H0975297 | A | 3/1997 |
| JP | H09238893 | A | 9/1997 |
| JP | 2005253543 | A | 9/2005 |
| RU | 133719 | U1 | 10/2013 |
| WO | WO 96/01132 | A1 | 1/1996 |

* cited by examiner

MEDICAL INSTRUMENT

CROSS-REFERENCE TO RELATED APPLICATION

This application claims priority to European Application No. 21209026.0, filed Nov. 18, 2021, the entirety of which is incorporated by reference herein.

TECHNICAL FIELD

Embodiments of the invention described herein relate to a medical instrument for medical or surgical treatment of a human or animal patient. Particularly embodiments of the invention refer to instruments comprising a light-conducting device that is configured to conduct light away from a site of action of the instrument or additionally or alternatively conduct light toward a site of action of the instrument.

BACKGROUND

From EP 2 113 190 A1 an arrangement is known consisting of a surgical instrument and trocar through the working channel of which the instrument can be moved. The instrument comprises a light-conducting device by means of which light can be received or emitted at the distal end of the instrument. The trocar is provided with one or multiple protection elements at its distal end that block the working channel and in this manner avoid entering of fluids into the working channel. The instrument can move the protection element away when it is moved in distal direction in order to obtain in this manner an unrestricted view of the target area of the instrument.

EP 3 195 824 A1 proposes an instrument having a channel in which an optical fiber is longitudinally movably arranged. The optical fiber comprises a light-emitting surface at its distal end from which a laser beam can exit. The channel is provided with a wiper element 21 at its distal end that closes the channel when the fiber is retracted and that avoids entering of fine fluid drops into the channel and the deposition thereof on the light exit surface of the fiber. During forward movement of the fiber the wiper element wipes the light exit surface and thus cleans it.

Additional prior art is formed by EP 1 773 223 B1 that illustrates a device for argon plasma coagulation, the gas-guiding channel of which is provided with a closure member.

SUMMARY

Applications exist in which the light-conducting device or another optical element of an instrument shall be or has to be immovably supported, such that it cannot be moved out of a contamination area.

Therefrom the object is derived on which the invention is based, according to which a possibility shall be provided to maintain an optical element of an instrument during use of the latter as clean as possible.

This object is solved by means of the instrument according to the appended claims.

The instrument according to an embodiment of the invention comprises an instrument body in which at least one channel is formed that comprises a distal end and a proximal end. Alternatively, such a channel can also be formed "on" the instrument, in that it is formed in a separate element that is coupled to the body of the instrument. The separate element channel could be coupled either directly or indirectly and may be connected by one or more clamps (e.g., springy clips). The following description applies for both embodiments.

The channel can extend particularly from the distal end of the instrument up to its proximal end at which a connection device can be configured to connect the proximal end of the instrument and therewith also the channel to a fluid source. The fluid source can be particularly configured to supply a gaseous fluid, such as air, a pure gas, e.g., nitrogen, argon, carbon dioxide or another desired gas, or mixed gas consisting of one or multiple gases. Thereby, the fluid source can be further configured to supply the gaseous fluid with a predefined pressure to adjust a predefined gas pressure and/or a predefined gas flow in the channel. The instrument body can comprise multiple channels to receive or discharge fluids at the distal end of the instrument. Particularly the instrument can comprise one or multiple gas supply channels and/or one or multiple suction channels.

The at least one channel comprises a fluid discharge opening at its distal end. This fluid discharge opening is concurrently a light passage opening in the instrument according to the invention through which light can enter and/or can exit. Preferably the light passage opening is facing a site of action of the instrument at which, for example, an electrode can be arranged held on the instrument. Also, multiple electrodes can be provided. One or more of such electrodes can be arranged immovably or movably on the instrument. In addition, the at least one electrode can be connected to an electrical source, e.g. a radio frequency voltage source, in order to influence biological tissue by means of current. Particularly the electrical source is configured to provide a voltage and a current that are so high that they are sufficient for spark creation on the electrode. For example, the electrode is a cutting electrode, the voltage a cutting voltage and the current flowing from the electrode to the tissue a cutting current. The created spark emits light that illuminates into the channel via the light passage opening.

In addition, an optical element comprising a light passage window is arranged inside the channel with distance to the distal end of the channel. The light passage window and therewith the optical element is immovably arranged inside the channel. For example, the optical element is immovably connected with the body of the instrument. In addition, the light passage window of the optical element is distanced from the light passage opening in proximal direction, the latter being realized by the gas discharge opening.

Between the light passage window and the light passage opening a closure device is arranged comprising a closure member that can be moved between an open position and a closed position. In its closed position the closure member is configured to block the channel against passage of particles and particularly liquid droplets and thus to shield the light passage window of the optical element from contamination. In the open position the closure member is further configured to release the channel for the passage of gases as well as for the passage of light. Particularly the closure member is not controlled by means of a movement of the optical element, even if the latter should be movably arranged inside the channel. There is no operation connection between the optical element and the closure device and particularly its closure member. Preferably the optical element and the closure member do not contact each other.

Further preferably the optical element is arranged in a non-varying distance from the light exit opening of the channel.

The optical element can comprise particularly a light-conducting device or can be realized by a light-conducting device. For example, the optical element can include one single optical fiber or a bundle of optical fibers, wherein the fiber or the fibers comprise respectively one light passage window at their respective distal end.

The light passage window can be used to radiate light for analytic and/or therapeutic purposes on the tissue to be treated. The light passage window can also be used to receive light created during treatment of the tissue, e.g. light of a spark burning between an electrode and the tissue, and to supply the light to a light analysis device. The light analysis can serve, for example, to identify the tissue that is subject to the treatment. Also other parameters (e.g. spark stability or similar) can be determined. For optical evaluation of the light, e.g. for tissue analysis, the optical emission spectroscopy (OES), the optical coherence tomography (OCT), Raman-spectroscopy, photoacoustical analysis or other optical methods can be used.

In different embodiments the closure member can respectively have one end that is immovably supported on the instrument, from which end the remaining part of the closure member extends away. The supported end can be immovably or movably connected with the instrument, e.g. pivotably connected. The remaining part of the closure member is thereby movably supported on the instrument and can therefore be moved back and forth between an open position and a closed position. The closure member can be rigid or elastic, stiff or slack.

Embodiments are possible that operate with only one single closure member. In addition, embodiments exist having multiple closure members that, for example, spread away from one another in the open position and are in abutment with each other in the closed position. The closure member or the closure members can be realized by bendable lamellae. They can be resiliently pretensioned to one another to define a cone or pyramid shape, whereby the lines of contact are the surface lines of the cone or edges of the pyramid. In the open position the lamellae can be spread away from one another. It is advantageous, if the lamellae consist of bending elastic material for this purpose. Additionally or alternatively, the closure member can be made of a stretchable material. For example, the closure member can then have the shape of a cone or pyramid having a small opening at its tip. The material is stretched accordingly for opening, so that the opening at the cone or pyramid is enlarged. The base of the pyramid or the cone can in all these embodiments correspond to the channel cross-section.

Preferably the closure member is arranged such that it blocks the channel in the rest position, whereby it can be transitioned by means of a pressure and/or the flow of the fluid, particularly gas, present inside the channel into the open position. To this extent the closure member can be configured to be pneumatically actuated. The channel can be a purge gas channel, whereby the gas pressure of the purge gas or other gas provided by the fluid source is sufficient to open the closure member.

Preferably the light passage window comprises a sight cone that extends through the fluid discharge opening and thus through the light passage opening. The closure member of the closure device is preferably configured, such that it blocks the sight cone in the closed position, however, unblocks it in the open position.

As described above, the closure device can be controlled by means of the fluid guided through the channel, particularly its pressure or flow velocity. The fluid acts directly on the closure member that is self-controlled to this extent. It is however also possible to provide an externally controlled closure device that is connected with a mechanical actuating device. For example, the mechanical actuating device can be an electromagnetic actuating device or a pneumatic actuating device or a manual actuating device. For example, the closure member can be mechanically connected with an actuating bottom of the instrument in order to be moved back and forth between the open position and the closed position respectively in a controlled manner. Also an electromechanical or pneumatic actuator can be provided for movement of the closure member between the open position and the closed position.

All embodiments have in common that, due to the control of the closure device either by means of the gas flow or by other actuating elements or actuating media, a release of the passage between the light passage opening and the light passage window is carried out in a controlled and piloted manner. The unblocking, i.e. the opening of the closure device, can particularly be limited to phases in which indeed a light passage is required. In addition, the instrument can be configured to open and to close the closure device synchronously with the supply of fluid, e.g. purge gas, to the site of action of the instrument. In addition, the instrument and/or its supplying apparatus can be configured to start the gas supply through the channel before activation of the RF electrode and to only terminate it after the end of the activation of the RF electrode. However, it can be guaranteed that the passage between the light passage window and the light passage opening is only unblocked, if also a gas flow directed into distal direction flows away from the light passage window, such that a contamination of the light passage window is avoided to a great extent. In case of missing gas flow, the closure device closes the passage from the light passage opening to the light passage window and in this way avoids the contamination of the light passage window. When the closure device is open, the contamination is avoided by means of the present gas flow that carries all contaminating particles or droplets away from the light passage opening.

The closure device can comprise a closure member that is resiliently pretensioned toward its closing position that can be and is transferred into the open position by means of an actuator or the gas flow itself. Alternatively, the suction device can be configured to actuate the closure device. For this purpose the instrument can comprise a suction channel that opens out in the proximity of the distal end of the instrument. An actuator connected to the suction channel is then configured to open and close the closure device depending on whether a negative pressure is present in the suction channel or not. The suction channel can be connected to a suction device that is configured to be synchronously activated with a generator supplying the electrode. The suction device can alternatively be configured to be activated prior to the activation of the generator and to be deactivated again only after the deactivation of the generator. In general, it is also possible to guarantee that a) the closure device is only open while the electrode is supplied with current or b) the closure device is only open while a purge flow directed in distal direction is established inside the purge channel or c) the closure device is only open while a flow is established in proximal direction inside the suction channel.

BRIEF DESCRIPTION OF THE DRAWINGS

Further advantageous details relating to embodiments of the invention are derived from the claims as well as the description and the assigned drawing with its figures that show the following:

DETAILED DESCRIPTION

Figure 1:
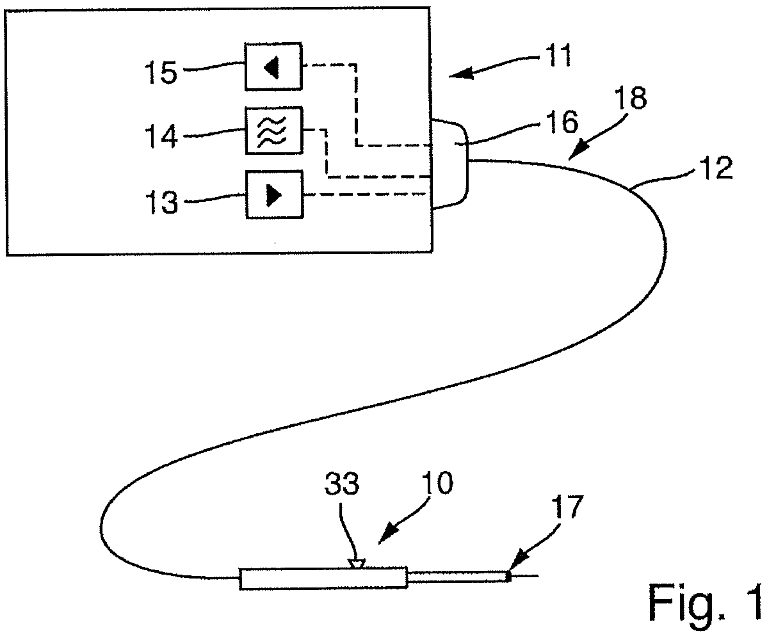
FIG. 1 a supplying apparatus with an instrument connected thereto in an overview illustration, FIG. 2 the distal end of the instrument according to FIG. 1 in a schematic cross-sectional illustration, FIGS. 3*a* and 3*b* a schematic illustration in part of the instrument with closure device in closed and open condition, and FIGS. 4*a* to 9*b* further embodiments of the instrument and its closure device in open position and closed position respectively.

FIG. 1 illustrates an instrument 10 according to the invention that is connected to a supplying apparatus 11. The apparatus 11 is connected with the instrument 10 via a respective line 12 and configured to supply the instrument 10 with at least one operating media. For this purpose the apparatus 11 can comprise one or more fluid sources 13, one or more electrical generators 14 and/or one or more suction devices 15 that are connected with line 12 or the instrument 10 respectively via one or more connectors 16. FIG. 1 illustrates instrument 10 as hand-held instrument for the open surgical use. The invention, however, also extends to otherwise configured instruments, e.g., instruments for laparoscopic use or probes, which can be inserted into the body of a patient through a working channel of an endoscope, a trocar or another access.

The instrument 10 comprises a distal end 17 as well as a proximal end 18, which proximal end 18 can be realized by connector 16 or a section of its line 12.

Figure 2:
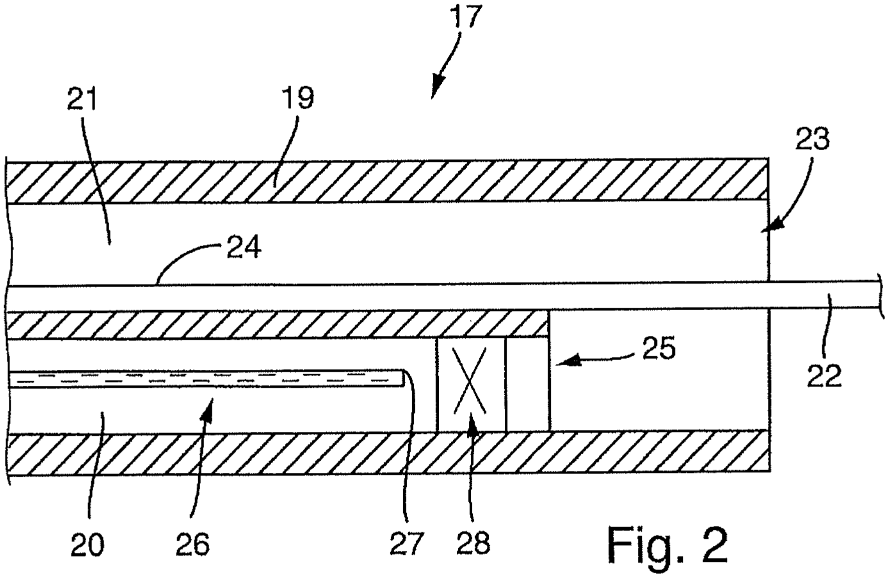

The distal end 17 of instrument 10 is separately illustrated in FIG. 2. It comprises the distal section of an instrument body 19 through which at least one channel 20 extends. The channel 20 is particularly a fluid-guiding channel, e.g., gas-guiding channel, which extends preferably from the distal end 17 through the instrument 10 (FIG. 1) and the entire line 12 (FIG. 1) up to the proximal end 18 (FIG. 1) or connector 16 (FIG. 1) and is connected to the gas source 13 (FIG. 1) there. As an option, instrument 10 can comprise additional channels, such as a suction channel 21 that also extends from the distal end 17 of instrument 10 up to its proximal end 18 or connector 16 and is connected to the suction device 15 there. As an option, other channels and/or additional channels can be provided to convey liquids and/or gases to the distal end 17 of instrument 10 or away therefrom and can let them enter or exit there.

The instrument 10 can comprise tools for influencing biological tissue. Such a tool can be an electrode 22, for example, that is held in or on the distal end 17 of instrument 10 and ends there or that projects from a gas passage opening or ends in short distance before the latter. The electrode 22 is coupled to generator 14 (FIG. 1) via an electrical line 24 that extends through the line 12 up to the proximal end 18 or connector 16. However, also multiple electrodes or other tools, such as a water jet tool, a laser tool or the like, can be provided.

The channel 20 comprises the distal opening that is a gas discharge opening and concurrently a light passage opening 25. Inside channel 20 an optical element 26, e.g., in form of an optical fiber, is preferably immovably arranged, which comprises a light passage window 27 at its distal end. The light passage window 27 can be formed by the face of the optical element 26, that is e.g., by the face of an optical fiber. The light passage window 27 and together with it the optical element 26 are preferably axially immovably arranged inside the channel 20. Preferably, the light passage window 27 is arranged with distance in proximal direction relative to the light passage opening 25.

A closure device 28 is arranged between the light passage window 27 and the light passage opening 25. The closure device 28 is configured to unblock or block the passage from the light passage opening 25 to the light passage window 27 in a controlled manner. Preferably, the closure device 28 is controlled by the gas flow inside channel 20 or also by other media, however, never by any movement of the optical element 26, which is preferably immovably arranged as mentioned.

Figure 3A:
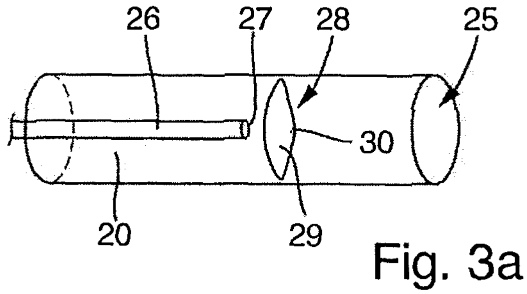
Figure 3B:
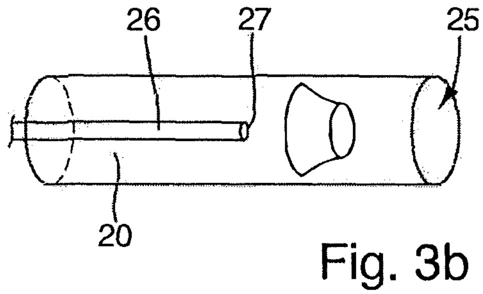

A first embodiment of the closure device 28 is apparent from FIGS. 3*a* and 3*b*. The closure device 28 is realized there by a substantially cone-shaped closure member 29 made of tensile elastic material that comprises an expandable opening at its tip 30. The tip 30 is facing the light passage opening 25. The opening at the tip 30 is very narrow or completely closed in the closed condition. The tensile elasticity of the material of closure member 29 is so high that the opening 30 can be stretched so wide by means of the pressure present inside channel 20 that the desired gas flow can exit from the light passage opening 25 and thus also the light path from the light passage opening 25 to the light passage window 27 is unblocked. If the gas flow is present, the closure member 29 is in open position.

The closure member 29 comprises a section immovably held on instrument 10. This section is realized in the closure member 29 by a circular section that defines the foot of the cone realized by the closure member 29. This section is immovably connected with the wall of channel 20. The remaining parts of the cone-shaped closure member 29 can be deformed in an elastic or flexible manner and are movable to this extent.

Figure 4A:
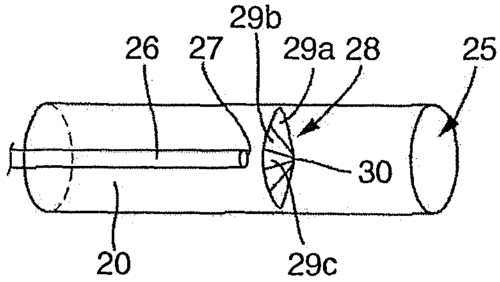
Figure 4B:
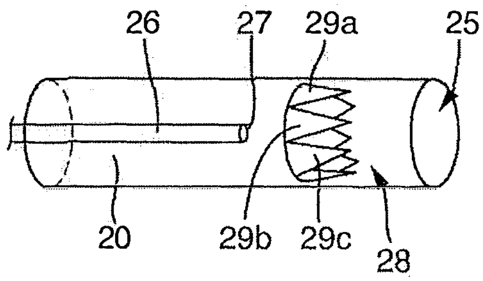

A modified embodiment is illustrated in FIGS. 4*a* and 4*b* to which the description above applies, except for the following particularities:

The closure device 28 comprises multiple closure members 29*a*, 29*b*, 29*c*, etc. that are flexible and form a cone, if they abut against one another with their edges. At its tip 30 the lamella-like closure members 29*a*, 29*b*, 29*c*, etc. join each other and therefore close the passage from the light passage opening 25 to the light passage window 27. However, if channel 20 is supplied with gas, the closure members 29*a*, 29*b*, 29*c* etc. spread as shown in FIG. 4*b*. Thus, the passage for gas as well as for light is unblocked by the closure device 28, the closure members 29*a*, 29*b* etc. are in open position.

The closure members 29*a*, 29*b*, 29*c*, etc. comprise a section immovably held on instrument 10. This section is realized in the closure members 29*a*, 29*b*, 29*c*, etc. by a portion of a circular section that defines the foot of the cone realized by the closure members 29*a*, 29*b*, 29*c*, etc. This section is immovably connected with the wall of channel 20. The remaining parts of the cone-shaped closure members 29*a*, 29*b*, 29*c*, etc. can be deformed in an elastic or flexible manner and are movable to this extent.

Figure 5A:
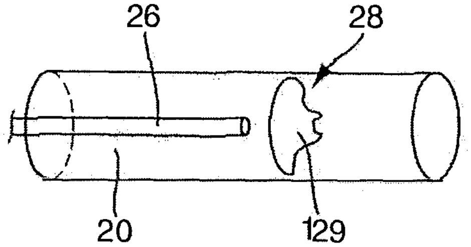
Figure 5B:
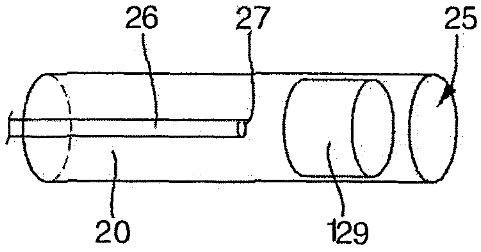

A further modified embodiment of the closure device 28 is illustrated in FIGS. 5*a* and 5*b* in which the closure member 129 is realized by a foldable, flexible, slack material, such as a foil hose section. Closure member 129 collapses without gas supply of channel 20 and blocks channel 20 as irregular-shaped body. In case of a gas flow, closure member 29' unfolds, as illustrated in FIG. 5*b*, and therefore unblocks the passage for light and gas between light passage window 27 and light passage opening 25. Apart therefrom, the description above applies accordingly.

The closure member 129 comprises a section immovably held on instrument 10. This section is realized in the closure member 129 by a section that defines the foot of the unfolded through-hole realized by the closure member 129. This section is immovably connected with the wall of channel 20. The remaining parts of the closure member 129 can be deformed in an elastic or flexible manner and are movable to this extent.

Figure 6A:
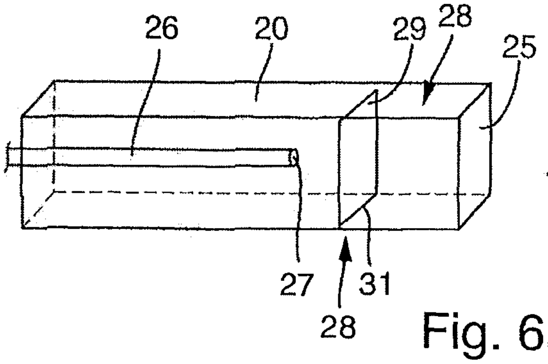
Figure 6B:
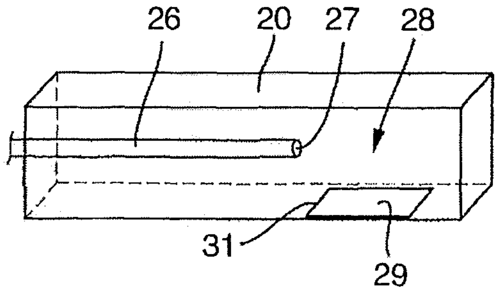

In the described embodiments of FIGS. 3*a* to 5*b* a channel with round cross-section has been taken as basis for graphical illustration. Just as well, however, in these embodiments channel 20 can have other cross-sections, e.g. polygonal cross-sections, such as triangle, rectangle, hexagon or polygon with curved edges. Only by way of example in FIGS. 6*a* and 6*b* a configuration of channel 20 and the closure device 28 having a rectangular cross-section is illustrated. Here closure device 28 comprises a closure member configured as flap, the circumference of which is equal to the cross-section of channel 20. The flap-like closure member 229 is connected with one edge 31 with the instrument or the wall of channel 20. Thereby edge 31 can be rigidly anchored and the closure member 229 can be configured to be flexible. Alternatively, the edge 31 can be realized in a hinge-like manner. In the blocking position according to FIG. 6*a*, the closure member 229 blocks channel 20 and thus the passage between the light passage window 27 and the light exit opening 25. The closure member 229 can be resiliently pretensioned toward this position. This resilient pretension can be provided by intrinsic elasticity of closure member 229 or by a separate spring element. A stop can be assigned to the closure member 229 against which it abuts in the blocking position (not illustrated). This is particularly advantageous in embodiments in which the closure member 229 is held at the edge 31 by means of a hinge. In FIG. 6*b* the open position of the closure device 28 is illustrated in which closure member 229 is displaced out of its rest position into the open position by means of gas flowing through the channel 20 in distal direction.

Figure 7A:
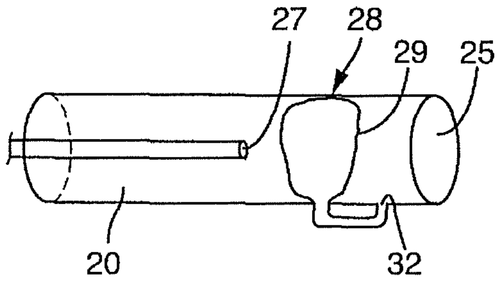
Figure 7B:
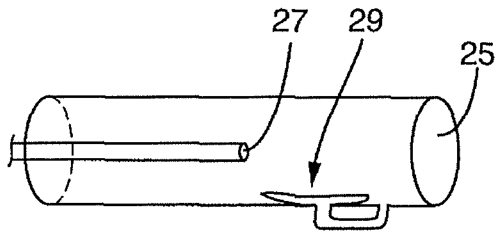

FIGS. 7*a* and 7*b* illustrate another embodiment of a fluid-actuated closure device 28. In this a balloon-like hollow closure member 329 is part of the closure device 28, wherein the closure member 329 is again arranged between the light passage window 27 and the light passage opening 25. The balloon-like closure member 329 is in fluid connection with a Venturi opening 32 arranged in the gas path through which the static pressure of the gas flow becomes effective. If the static pressure decreases, due to the velocity of the gas flow, collapse of the balloon-like closure member 29 results such that the closure member 329 unblocks the gas path, as illustrated in FIG. 7*b*.

In a preferred embodiment the balloon-like closure member 329 or an actuator for actuating the closure member 329 is connected to the suction channel 21. Thereby a negative pressure of the suction can be used for actuating the closure device 28. For this purpose a transverse bore can be provided on the level of element 28 to element 21 (FIG. 2). Thereby a robust system is created. Particularly, larger pressure differences and thus large actuating forces can be created.

In such an embodiment, preferably the suction device 15 and the purge gas source 13 are synchronized with the RF generator 14. This reduces the sound pressure load that would be otherwise too high during continuous operation.

Figure 8A:
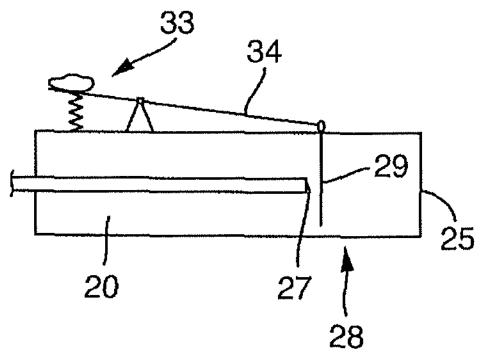
Figure 8B:
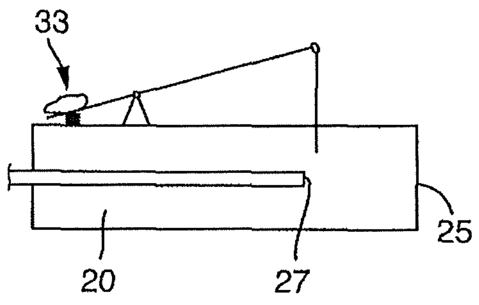

All embodiments described above have in common that the closure members (FIGS. 3*a* through 7*b*) of the closure device 28 is controlled pneumatically due to the effect of the gas or its flow inside channel 20. It is however also possible to externally control the closure device 28, as shown in FIGS. 8*a* and 8*b* in a simple first example. There, instrument 10 comprises an actuating device 33 that is only illustrated schematically and that can be realized by means of an actuating button on the instrument 10, for example. The actuating device 33 can thereby be provided to activate or deactivate instrument 10 and thus the connected generator 14. The actuating device 33 can additionally or alternatively also be configured for triggering other activation or switching processes, e.g. for triggering a spectral analysis of the light originating from the spark of the electrode. Concurrently the actuating device can move the closure member 29 via a suitable transmission, that is here only schematically illustrated by means of a two-arm lever 34, such that it blocks the passage between the light passage window 27 and the light passage opening 25 in the closed position according to FIG. 8*a* and unblocks it in the actuated position according to FIG. 8*b*.

Figure 9A:
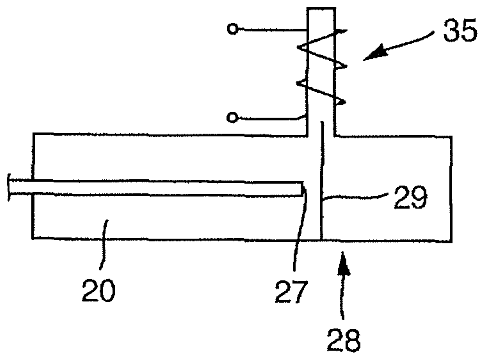
Figure 9B:
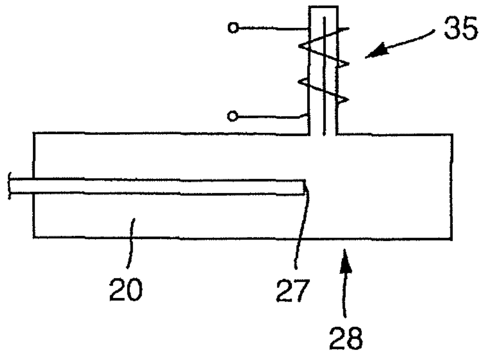

As apparent from the example of FIGS. 9*a* and 9*b*, the actuation of the closure device 28 can also be carried out by means of other actuators, e.g. by means of a magnetic actuator 35 with which the closure member 29 can be positioned in the closed position according to FIG. 9*a* inside channel 20 and in open position, as shown in FIG. 9*b*, outside channel 20.

The instrument 10 of FIG. 1 according to the invention operates as follows:

For application on a patient instrument 10 is moved toward the operation site and is activated by actuation of a suitable switch, e.g., the actuating device 33. Alternatively, other switching means can serve for activation, e.g., foot switches or other operating devices. The apparatus 11 thereby receives a respective switching impulse and activates the respectively addressed or present devices, such as gas source 13, electrical generator 14 and/or suction device 15. If the instrument 10 is an electrosurgical instrument, typically the gas source 13 is activated before the generator 14 is activated. As long as the gas source 13 is not activated, i.e., channel 20 is not supplied with gas, the closure device 28 is closed. As soon as a respectively sufficient gas pressure and/or a gas flow is established inside channel 20, the closure device 28 opens at least, if one of the embodiments according to FIGS. 3*a* to 7*b* is used.

After activation of generator 14 light originating from electrode 22 is received by optical element 26. Electrode 22 is preferably located in the field of view of the optical element 26 that is in the sight cone originating from the light passage window 27 and extending through the light passage opening 25. Spark light originating from the electrode can be detected and can be further conveyed from the optical element 26 to an analysis device, e.g. a spectral analysis device, that can be part of instrument 10 or that can be configured and arranged separately.

The gas flow forwarded through channel 20 and discharged from light passage opening 25 effectively avoids disposal of particles, droplets or other contamination on the light passage window 27. However, as soon as the gas flow comes to a halt, e.g. because it has been interrupted, the closure device 28 closes. Even if contamination is continuously created due to turbulences or the like, e.g. due to the activation of the suction device 15, that sucks liquids or other matter from the operation area via suction channel 21, the light passage window 27 remains sealed off and spared from contamination. This also applies, if it is continued to operate with electrode 22 without gas supply through channel 20 and particles are released in this manner.

The embodiments of instrument 10 illustrated in FIGS. 8*a* to 9*b* operate in similar manner. In the embodiments according to FIGS. 8*a* and 8*b*, the closure device 28 is always unblocked, if the actuating device 33 is activated. The activation of actuating device 33 can be carried out independent from the activation of apparatus 11 (FIG. 1) and generator 14 (FIG. 1). For example, channel. 20 can be supplied with gas under low pressure. If closure device 28 is closed, it can concurrently block the gas flow and the light passage. The closure device 28 also blocks the passage of contamination. As soon as the closure device 28 is opened by means of the actuating device 33, the light path is unblocked. Concurrently, the gas flow is released that avoids entering of contamination. If a gas flow shall also be possible, if the closure device 28 is closed, a bypass can be provided parallel to the closure device 28 that is opaque to light.

In embodiments according to FIGS. 9*a* and 9*b*, closure device 28 is actuated by means of the magnetic actuator 35 or another suitable electrical actuator. Application of current to actuator 35 can be carried out synchronously with the application of current of electrode 22 or independent therefrom. The latter, for example, if light from the electrode 22 shall be received only occasionally. The apparatus 11 in connection with instrument 10 is then configured such that spectrometer and actuator 35 are concurrently activated for receiving light from the treatment site, e.g. for spectral analysis of light. Thereby the light passage window 27 is permanently protected from contamination. In the activated condition the gas flow flowing through channel 20 avoids contamination. In case of deactivation, closure device 28 closes and closes the light passage window 27. This principle applies for all embodiments.

The invention is not limited to electrosurgical instruments. It can also be used for laser surgical instruments or cryosurgical instruments. In the case of laser surgery, the optical element 26 can be configured to emit a laser beam out of the light passage window 27 through the light passage opening 25 toward the tissue. The gas flow inside channel 20 keeps the light passage window 27 free from contamination in the activated case. In the case of deactivation the closure device 28 closes, e.g. according to the principles of FIGS. 8*a* to 9*b*.

Instrument 10 can also be a water jet surgical or other instrument. In addition or as an alternative to the electrode 22, then a water injection channel can be provided in order to treat respective tissue at the operation site, preferably in the field of view of optical element 26. Apart therefrom the description above applies accordingly.

An instrument according to the invention for medical or surgical treatment of a human or animal patient comprises at least one tool suitable for influencing a patient, e.g. an electrode 22, which is or are located in the field of view of an optical element 26. The optical element 26 is arranged inside a channel 20 in which a fluid flow can be maintained or can be caused in distal direction. The light passage window 27 of optical element 26 is offset in proximal direction relative to the distal opening 25 of channel 20. A closure device 28 is arranged between light passage window 27 and opening 25 of channel 20, which blocks passage of substances, particularly passage of liquid droplets and particles, from the opening 25 to the light passage window 27 as long as it is in closed position. If the closure device 28 is open, it unblocks the fluid path and the light path between the light passage window 27 and the opening 25. Preferably the closure device 28 is controlled pneumatically by means of the liquid or gaseous fluid flowing inside channel 20. With this measure a contamination of the light passage window 27 during operation of the instrument 10 can be reliably avoided or at least reduced to a minor degree.

The invention claimed is:

1. An instrument for medical or surgical treatment of a human or animal patient, comprising:

an instrument body in or on which at least one channel is formed that comprises a distal end and a proximal end, wherein the channel is a fluid channel adapted to be connected to a fluid source at its proximal end and comprises an opening at its distal end;

an optical element that comprises at least one light passage window that is immovably arranged inside the channel; and a closure device that is arranged inside the channel between the light passage window and the distal end of the fluid channel and that comprises at least one closure member that can be moved between an open position and a closed position, wherein a site cone is defined by the light passage window and extends through the opening in a distal direction, and the closure member is configured to block the sight cone in the closed position and to unblock it in the open position.

2. The instrument according to claim 1, characterized in that the closure member comprises an end immovably supported on the instrument.

3. The instrument according to claim 1, characterized in that the closure device comprises multiple closure members that are respectively pivotably supported at one end on the instrument.

4. The instrument according to claim 1, characterized in that the closure device comprises multiple bending elastic lamellae.

5. The instrument according to claim 1, characterized in that the closure member is an element made of a stretchable material.

6. The instrument according to claim 1, characterized in that the closure member is arranged such that it can be actuated by fluid flowing through the fluid channel.

7. The instrument according to claim 1, characterized in that the channel can be connected to a gas source as fluid source.

8. The instrument according to claim 1, characterized in that the instrument comprises at least one additional channel for supply or discharge of fluids.

9. The instrument according to claim 1, characterized in that the instrument comprises an electrode.

10. The instrument according to claim 9, characterized in that the electrode is arranged within or in front of the opening.

11. The instrument according to claim 9, characterized in that the electrode is arranged at least partly within the sight cone.

12. The instrument according to claim 1, characterized in that the closure device is connected with a mechanical actuating device.

13. The instrument according to claim 1, characterized in that the closure device is connected with an electromagnetic actuating device.

14. The instrument according to claim 1, characterized in that the closure device is connected to a pneumatic Venturi actuating device.

* * * * *